US006384270B1

(12) United States Patent
Ancel et al.

(10) Patent No.: US 6,384,270 B1
(45) Date of Patent: May 7, 2002

(54) METHOD FOR PREPARING VITAMIN A

(75) Inventors: Jean-Erick Ancel, Saint Genis Laval; Pierre Meilland, Chaponost, both of (FR)

(73) Assignee: Aventis Animal Nutrition, S.A., Antony (FR)

( * ) Notice: Subject to any disclaimer, the term of this patent is extended or adjusted under 35 U.S.C. 154(b) by 0 days.

(21) Appl. No.: 09/743,289

(22) PCT Filed: Jul. 7, 1999

(86) PCT No.: PCT/FR99/01635

§ 371 Date: Apr. 20, 2001

§ 102(e) Date: Apr. 20, 2001

(87) PCT Pub. No.: WO00/02854

PCT Pub. Date: Jan. 20, 2000

(30) Foreign Application Priority Data

Jul. 10, 1998 (FR) .............................. 98 08873

(51) Int. Cl.[7] .......................... C07C 67/00; C07C 47/11
(52) U.S. Cl. .................... 560/259; 568/447; 568/824
(58) Field of Search ................. 568/346, 347, 568/348, 349, 354, 356, 361, 364, 365, 378, 447, 824; 560/259

(56) References Cited

U.S. PATENT DOCUMENTS

| 3,057,888 A | 10/1962 | Marbet et al. ......... 260/397.47 |
| 5,449,844 A | 9/1995 | Ancel et al. ................. 568/691 |
| 5,563,297 A | 10/1996 | Bienayme ................... 568/314 |
| 5,567,852 A | * 10/1996 | Bienayme et al. .......... 568/378 |
| 5,639,919 A | 6/1997 | Bienayme ................... 568/446 |

FOREIGN PATENT DOCUMENTS

| DE | 11 76 125 | 8/1964 |
| EP | 0 544 588 | 6/1993 |
| EP | 0 647 623 | 4/1995 |

OTHER PUBLICATIONS

Bienayme, H., "Efficiency of Organometallic Catalysis in a New 'Ecological' Synthesis of Retinal;" Tetrahedron Letters, vol. 35 (40), pp. 7383–7386 (1994).

* cited by examiner

Primary Examiner—Sreeni Padmanabhan
(74) Attorney, Agent, or Firm—Connolly Bove Lodge & Hutz LLP

(57) ABSTRACT

The invention relates to a process for making vitamin A from ethynyl-retro-α-ionol using an allene acetate as intermediate.

33 Claims, No Drawings

METHOD FOR PREPARING VITAMIN A

This is the National Stage Application of PCT/PR99/01635 filed Jul. 7, 1999 now WO 00/02854 published Jan. 20, 2001.

The present invention relates to a novel method for preparing vitamin A and to novel intermediates obtained using this method.

It is known according to the patent application published under the number EP-A-0647623 to prepare vitamin A from ethynyl-retro-α-ionol carbonate and 2-methylbutadiene followed by rearrangement into an allene derivative in the presence of a rearrangement catalyst chosen from nickel and/or palladium in the presence of a phosphine. The last step consists in isomerizing the product obtained in the preceding step to retinal. This method has several disadvantages from the industrial point of view; on the one hand, the preparation in the first step of a carbonate whose preparation yield is not excellent and, on the other hand, the second step has rearrangement yields which are not excellent either and requires the use of an expensive rearrangement catalyst which makes the method difficult to exploit industrially.

The present invention has made it possible, starting with ethynyl-retro-α-ionol, to directly obtain an allene derivative without preparing the carbonate intermediate. This reaction is carried out in the presence of a metal catalyst.

It is known in the prior art, for example according to patents FR 1 554 805 and FR 2 135 550, to carry out the isomerization of propargyl alcohols to α,β-ethylenic aldehydes using either catalysts based on alkyl orthovanadates or silyl orthovanadates. Unfortunately, this type of catalyst has no action on ethynyl-retro-α-ionol.

The present invention relates to the preparation of a C15 intermediate of vitamin A of formula:

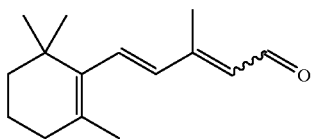

where, in a first step, the ethynyl-retro-α-ionol is acetylated, in a second step, the ethynyl-retro-α-ionol acetate is isomerized to allene acetate and in a final step, the compound obtained in the second step is hydrolyzed. The first step may be schematically represented in the following manner:

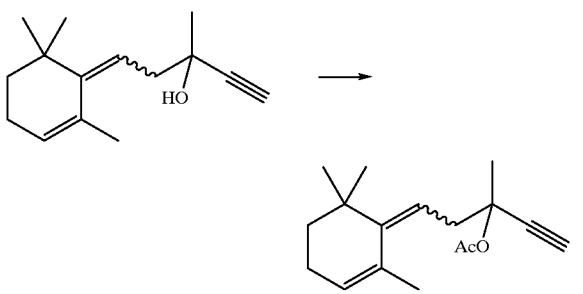

The preparation of propargyl acetate is carried out by bringing ethynyl-retro-α-ionol into contact with acetic anhydride or acetyl chloride in the presence of a tertiary amine. Triethylamine, trimethylamine, tributylamine or pyridine is preferably used as tertiary amine. An activating agent such as dimethylaminopyridine is preferably added. The quantity of activating agent which is used is preferably between 1 and 5%, calculated in molar equivalent relative to the alcohol. It is preferable to work in an inert solvent which is chosen in particular from optionally halogenated aromatic or aliphatic solvents.

The second step, which consists in isomerizing the propargyl acetate obtained in the receding step, is carried out in the presence of a copper-based metal catalyst according to the following reaction scheme:

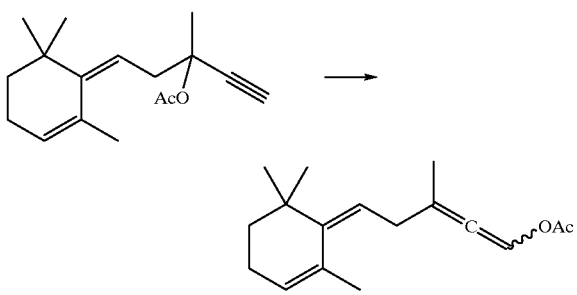

The catalysts used in the prior art and in particular in patent EP-A-0 647 623 based on palladium and/or on nickel, which-allow the formation of allenes from carbonates, are not active in the context of the present invention or give a completely degraded reaction mixture.

The use of copper(I) chloride is preferred.

For a better implementation of the invention, a molar ratio of copper(I) salt to propargyl acetate of between 0.5% and 5%, and preferably of about 1% is used. The reaction solvent is preferably chosen from the optionally halogenated aromatic or aliphatic solvents and esters. Monochlorobenzene is preferably used.

The optimum concentration of propargyl acetate in the reaction solvent is between 0.1 and 1 mol per liter and more preferably about 0.5 mol per liter.

The temperature conditions are chosen within limits which do not cause degradation of the propargyl acetate. It is preferable to work at temperatures of between 100 and 150° C. and preferably at about 100° C.

The allene intermediate of the following formula is a novel compound:

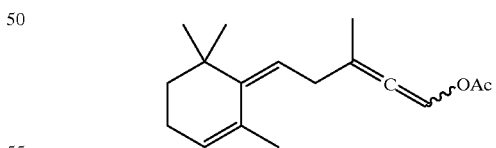

The next step consists in hydrolyzing the allene acetate to the corresponding aldehyde according to the following reaction:

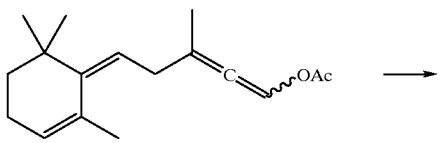

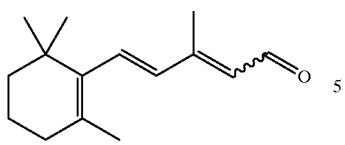

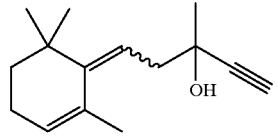

This reaction is carried out in the presence of an acid in a ketone solvent or in an aromatic solvent which is in particular halogenated. The isomerization and deacetylation catalyst is an inorganic acid chosen in particular from hydrochloric acid, hydrobromic acid or sulfuric acid. The use of hydrobromic acid in acetone is preferred.

According to a better way of carrying out the invention, the use of 0.25 to 0.5 equivalent of hydrobromic acid per mol of allene acetate is preferred.

Starting with the C15 aldehyde obtained in the preceding step, vitamin A is prepared according to a known method. There may be mentioned among the known methods patent FR 2,707,633 which, by condensation with a lithium or potassium salt of prenal dienolate, makes it possible to obtain a dihydropyran intermediate which, by controlled hydrolysis in the presence of a weak acid, leads to retinal.

It is also known according to the article by Krasnaya and Kucherov which appeared in Izvestiya Akademii Nauk SSSr, Otdelenie Khimicheskikh Nauk, No 6, pp 1160–1161 to condense the C15 aldehyde in acetal form with ethcxy-isoprene in the presence of zinc chloride, followed by the hydrolysis of the acetal with an acid and the removal of the ethoxy group.

The present invention also relates to a method for preparing for preparing vitamin A starting with β-ionone.

This method consists, in a first step, in isomerizing the β-ionone to retro-α-ionone in the presence of potassium tert-butoxide in dimethyl sulfoxide as for example described by Cerfontain in Synthetic Communications, 1974, 4(6), 325–30. This method relates more generally to the isomerization of β-ionone with a strong base chosen from alkali metal alcoholates or alkali metal hydroxides, in a polar aprotic solvent. The alkali metal alcoholate is preferably sodium methoxide; the alkali metal hydroxide is preferably sodium hydroxide, potassium hydroxide, lithium hydroxide, calcium or barium hydroxides. The solvent is in particular chosen from dimethyl sulfoxide, N-methylpyrrolidone or dimethylformamide. It is preferable to use a molar ratio between the strong base and the β-ionone of between 1 and 1.5. As regards the reaction conditions, it is preferable to work below room temperature and preferably between −10° C. and 20° C.

The second step consists in carrying out an ethynylation cf the retro-α-ionone obtained above according to the following reaction scheme:

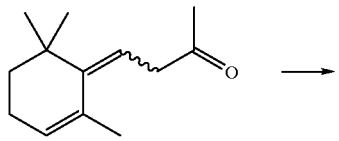

This step is carried out in the presence of lithium or magnesium acetylide. The use of magnesium acetylide formed in situ by bringing acetylene into contact with isopropylmagnesium chloride is preferred. As solvent, the use of ethers, polar solvents such as aromatic solvents is preferred; the use of tetrahydrofuran is most particularly preferred. The reaction temperature is preferably less than room temperature. It is in particular between −10° C. and room temperature. The reaction is preferably carried out in a solvent chosen from ethers, polar solvents such as aromatic solvents; the use of tetrahydrofuran is most particularly preferred.

The ethynyl-retro-α-ionol is then acetylated in accordance with the first step of the first method according to the invention, the propargyl acetate obtained is, according to the overall method for preparing vitamin A, condensed with a 1-methylbutadiene derivative according to the following reaction scheme:

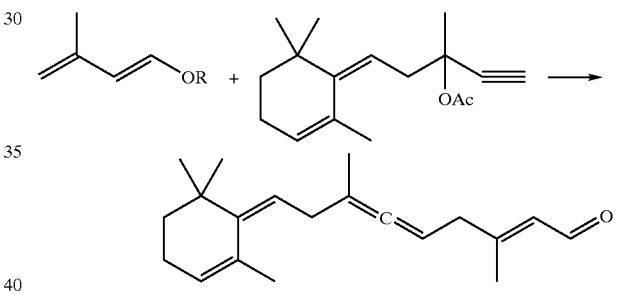

in which R represents a linear or substituted C1–C4 alkyl group, a linear or substituted C1–C4 acyl group or a trialkylsilyl or triarylsilyl group. The use of acetyl-1-methylbutadiene or 3-trimethylsilyloxy-1-methylbutadiene is preferred. The condensation reaction is preferably carried out in the presence of a Lewis acid chosen in particular from zinc chloride, titanium tetrachloride, boron trifluoride or the trityl salts (perchlorate, tetrafluoroborate). For a better implementation of the invention, the use of a solvent chosen from polar solvents such as nitroalkanes or chlorinated solvents is preferred. As regards the reaction conditions, the use of temperatures between −50° C. and +20° C., preferably between −30 and 0° C., is preferred.

The derivative thus obtained, which is an isomer of vitamin A, is isomerized to vitamin A under the same conditions as above according to the following scheme:

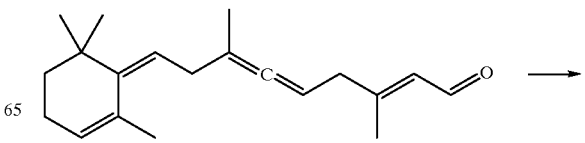

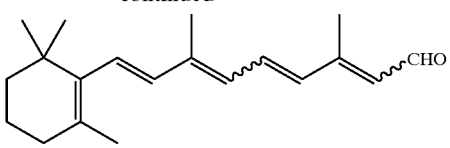

This reaction is carried out in the presence of an acid, in a ketone solvent or in an aromatic solvent which is in particular halogenated. The isomerization catalyst is chosen from inorganic acids such as in particular hydrochloric acid, hydrobromic acid or sulfuric acid. The use of hydrobromic acid in acetone is preferred.

According to a better way of carrying out the invention, it is preferable to use 0.25 to 0.5 equivalent of hydrobromic acid per mol of C20 allene derivative to be isomerized.

The all-trans-retinal is then obtained by rectifying with the iodine-hydroquinone complex according to U.S. Pat. No. 2,683,746.

The present invention will be described more fully with the aid of the following examples which should not be considered as limiting the invention.

EXAMPLE 1

First step: Acetylation of Ethynyl-Retro-α-ionol

Reaction:

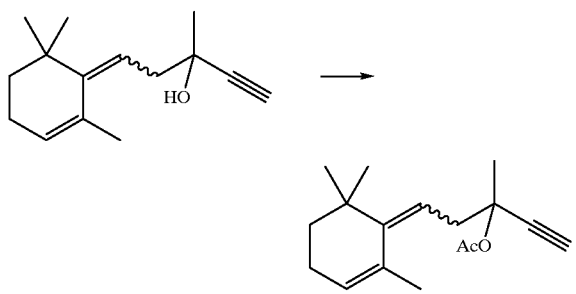

Load:
 Propargyl alcohol: 5.54 g, that is 25.37 mmol
 Acetic anhydride: 4.25 ml
 Triethylamine: 6.5 ml
 Dimethylaminopyridine: 190 mg, that is 0.06 eq
 Pentane: 75 ml Procedure:
 The following are successively introduced, under a nitrogen stream, into a 250 ml one-necked reactor, with magnetic stirring: the alcohol, the pentane, the amine, the anhydride and DMAP. The mixture is kept stirring for 10 hours at 20° C. and then 75 ml of ethyl ether are added, the organic phase is washed with water, dried over magnesium sulfate, filtered and concentrated.

Result:
 6.507 g of the expected acetate are obtained.
 Weight yield 98%. Titer 95%, determined by gas chromatography.

Second step: Isomerization of Ethynyl-Retro-α-ionol Acetate

Reaction:

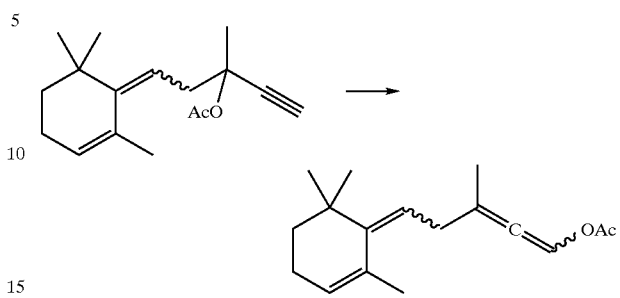

Load:
 7.944 g of propargyl acetate, that is 30.5 mmol
 34.6 mg of copper(I) chloride, that is 1.1%
 60 ml of chlorobenzene Procedure:
 The following are successively introduced, under an argon stream, into a 100 ml three-necked flask, provided with a thermometer, a reflux condenser and a magnetic stirrer: the acetate, chlorobenzene and then copper(I) chloride. The mixture is heated for 5 h at 110° C. and then cooled to 20° C. 200 ml of pentane are added, which causes crystallization of the copper(I) salt (quantity recovered: 31 mg, that is 85% of theory). The organic phase (filtrate) is concentrated under vacuum.

Result:
 8.193 g of a mixture of the expected allene acetate and chlorobenzene are obtained in the respective proportions 87/13, that is a dose yield of 90%.
 The same reaction was carried out in the presence of various quantities of copper(I) chloride; the results are indicated in the following table

| TESTS | QUANTITY OF CuCl | RESULTS |
| --- | --- | --- |
| 1 | 0.8 | AY = 62% |
| 2 | 0.6 | RC = 95% AY = 53% |
| 3 | 1.17 | RC = 97% AY = 68% |

In the above table, RC is understood to mean the rate of conversion of the initial product, that is to say of the prenyl acetate, and AY is understood to mean the actual yield of the reaction, that is to say the quantity of product obtained over the quantity of reagent introduced.

Third step: Hydrolysis of the allene acetate to a $C_{15}$ aldehyde

Reaction:

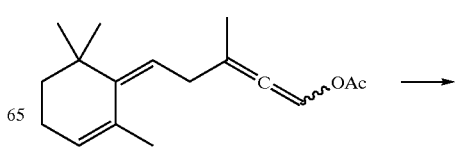

-continued

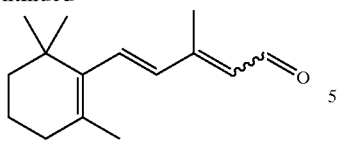

Load:
- 4.375 g of allene acetate having a titer of 87%, that is 14.6 mmol
- 400 microliters of an aqueous solution at 48% hydrobromic acid, that is 0.25 eq.
- 100 ml of acetone Procedure:
The following are successively introduced, under a nitrogen stream at 0° C., into a 250 ml one-necked round-bottomed flask provided with magnetic stirring: the allene acetate, acetone and then hydrobromic acid. After 4 hours of reaction, the acetone is evaporated under vacuum at 20° C. and then 70 ml of ether are added and the organic phase is washed with 3 times 50 ml of water. This phase is dried over magnesium sulfate, filtered and concentrated at cold temperature. The residue is chromatographed on silica gel.

Result:
1.834 g of clean aldehyde are obtained, that is a yield of 50% relative to the allene used.

Other tests of hydrolysis of allene acetate are carried out which are indicated in the following table:

| TESTS | Cata (eq) | solvent (mol/l) | conditions | yield of isolated material |
|---|---|---|---|---|
| 1 | HCl (0.5) | Acetone (0.32) | 24 h at 20° C. | 40% |
| 2 | HCl (0.16) | Acetone (0.3) | 6 h at 60° C. | 25% |
| 3 | HCl (0.5) | dioxane (0.33) | 6 h at 60° C. | 50% |

EXAMPLE 2

Preparation of vitamin A

1st step Isomerization of β-ionone to retro-α-ionone

Test 1—4914 mg of beta-ionone are poured over a suspension of 1733 mg of sodium methoxide in 23 ml of NMP, over 34 min, at 3° C. 70 min after the end of the pouring, the conversion is complete. The mixture is poured over 100 g of ice and extracted with twice 50 ml of diethyl ether, dried over magnesium sulfate and concentrated. 88% of retro-alpha-ionone is thus recovered for a 99% conversion of beta-ionone.

Test 2—4982 mg of beta-ionone are poured over a suspension of 1061 mg of sodium hydroxide in 23 ml of NMP, over 32 min. at 5° C. 15 h 30 min after the end of the pouring, the mixture is poured over 100 g of ice and extracted with twice 50 ml of ethyl ether, dried over magnesium sulfate and concentrated. 64% of retro-alpha-ionone is thus recovered, for an 88% conversion of beta-ionone.

Test 3—4923 mg of beta-ionone are poured over a suspension of 1813 mg of potassium hydroxide in 23 ml of NMP, over 32 min, at 5° C. 6 h 30 min after the end of the pouring, the mixture is poured over 100 g of ice and extracted with twice 50 ml of ethyl ether, dried over magnesium sulfate and concentrated. 83% of retro-alpha-ionone is thus recovered, for a 96% conversion of beta-ionone.

2nd Step Ethynylation of the Retro-α-ionone

An acetylene stream is passed through 20 ml of THF cooled to 8° C. (flow rate 100 ml/min), and then after 10 min, 27 ml of a 2M solution of isopropyl-magnesium chloride in THF at 8° C. are introduced therein over 25 min. At the end of the pouring, the mixture is left for 2 h 30 min under an acetylene stream and then heated to 5° C. and a solution of 4870 mg of retro-alpha-ionone in 10 ml of THF is poured in over 8 min. The temperature is increased to between 10 and 20° C. and then the mixture is kept stirring for 1 h 30 min. 20 ml of 0.2 N HCl at 4° C. are poured in and the mixture is extracted with twice 30 ml of ethyl ether, washed with water to neutrality and dried over magnesium sulfate. 67% of the expected ethynyl-retro-alpha-ionol is thus isolated.

3rd step Acetylation of Ethynyl-retro-α-ionol

It is carried out in accordance with step 1 of example 1.

Propargyl alcohol: 5.54 9g, that is 25.37 mmol
Acetic anhydride: 4.25 ml
Triethylamine: 6.5 ml
Dimethylaminopyridine: 190 mg, that is 0.06 eq
Pentane: 75 ml Procedure:
The following are successively introduced, under a nitrogen stream, into a 250 ml one-necked reactor, with magnetic stirring: the alcohol, the pentane, the amine, the anhydride and DMAP. The mixture is kept stirring for 10 hours at 20° C. and then 75 ml of ethyl ether are added, the organic phase is washed with water, dried over magnesium sulfate, filtered and concentrated.

Result:
6.507 g of the expected acetate are obtained. Weight yield 98%. Titer 95%, determined by gas chromatography.

4th Step Condensation of Acetyl-retro-α-ionol or Propargyl Acetate with a 1-methylbutadiene Derivative Reaction:

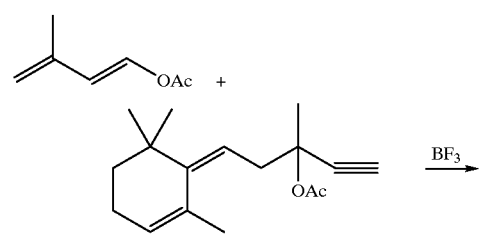

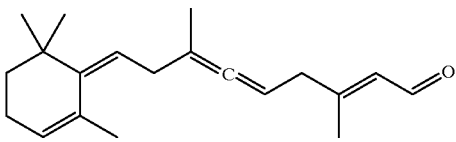

Procedure:

0.05 eq of boron trifluoride etherate is rapidly added to a mixture of 260 mg of C15 propargyl acetate (1 mmol) and 139 mg of methylbutadiene acetate (1.1 eq) in 5 ml of dichloromethane, cooled under argon at 0° C., and then the reaction medium is treated (after 1 hour at 0° C.) with 10 ml of a saturated aqueous solution of sodium hydrogen carbonate, and the organic matter is extracted with 10 ml of dichloromethane. After drying over magnesium sulfate and concentrating, 173 mg of the expected C20 aldehyde are separated on silica (that is a yield of 61% isolated). Being unstable, this C20 compound is rapidly isomerized to RETINAL, by the action of hydrobromic acid, according to:

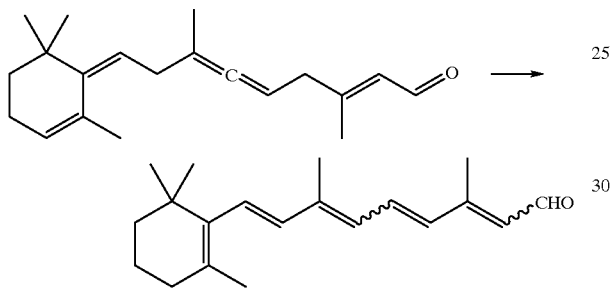

What is claimed is:

1. A method for preparing an intermediate of vitamin A of formula:

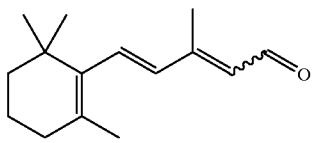

wherein, in a first step, ethynyl-retro-α-ionol is acetylated, in a second step, the ethynyl-retro-α-ionol acetate is isomerized to allene acetate and, in a final step, the compound obtained in the second step is hydrolyzed.

2. The method as claimed in claim 1, wherein the first step is carried out by bringing ethynyl-retro-α-ionol into contact with acetic anhydride or acetyl chloride in the presence of a tertiary amine.

3. The method as claimed in claim 2, wherein the tertiary amine is triethylamine, trimethylamine, tributylamine or pyridine.

4. The method as claimed in claim 2, wherein an activating agent such as dimethylamino pyridine is added.

5. The method as claimed in claim 2, wherein an inert solvent chosen from optionally halogenated aromatic or aliphatic solvents is used.

6. The method as claimed in claim 1, wherein the second step is carried out in the presence of a copper-based metal catalyst.

7. The method as claimed in claim 6, wherein copper(I) chloride is used.

8. The method as claimed in claim 6, wherein a molar ratio of copper (I) salt to ethynyl-retroα-ionol acetate of between 0.5% and 5% is used.

9. The method as claimed in claim 6, wherein the reaction solvent is chosen from the optionally halogenated aromatic or aliphatic solvents and esters.

10. The method as claimed in claim 9, wherein the solvent is monochlorobenzene.

11. The method as claimed in claim 6, wherein the concentration of propargyl acetate in the reaction solvent is between 0.1 and 1 mol per liter.

12. The method as claimed in claim 6, wherein the temperature used does not cause degradation of the propargyl acetate.

13. The method as claimed in claim 12, wherein the temperature is between 100 and 150° C.

14. An allene acetate of formula:

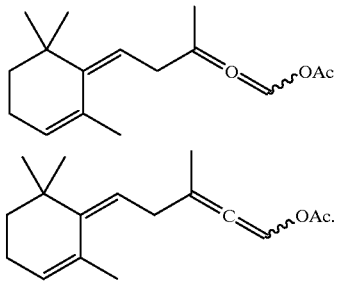

15. The method as claimed in claim 1, wherein the third step is carried out in the presence of an acid in a ketone solvent or in an aromatic solvent.

16. The method as claimed in claim 15, wherein the isomerization and deacetylation catalyst is an inorganic acid chosen from hydrochloric acid, hydrobromic acid or sulfuric acid.

17. The method as claimed in claim 15, wherein the reaction is carried out in the presence of hydrobromic acid in acetone.

18. A method for preparing vitamin A, wherein in a first step β-ionbne is isomerized to retro-α-ionone in the presence of a strong base chosen from alkali metal alcoholates or alkali metal hydroxides in a polar aprotic solvent, in a second step ethynylation of the compound obtained in the first step is carried out in the presence of magnesium or lithium acetylide to form ethynyl-retro-α-ionol, in a third step acetylation of the ethynyl-retro-α-ionol is carried out by bringing the ethynyl-retro-α-ionol into contact with acetic anhydride or acetyl chloride in the presence of a tertiary amine, in a fourth step the compound obtained in step three is condensed with an ether or an ester of methylbutadiene in the presence of a Lewis acid and in a fifth step the compound obtained in step four is isomerized in the presence of an inorganic acid.

19. The method as claimed in claim 18, wherein in the first step, the base is chosen from alkali metal alcoholates and alkali metal hydroxides.

20. The method as claimed in claim 18, wherein the molar ratio between the base and the β-ionone is between 1 and 1.5.

21. The method as claimed in claims 18, wherein the solvent is chosen from dimethyl sulfoxide, N-methylpyrrolidone or dimethylformamide.

22. The method as claimed in claim 18, wherein in the second step, the magnesium acetylide is formed in situ by mixing acetylene and isopropylmagnesium chloride.

23. The method as claimed in claim 18, wherein the solvent used is chosen from ethers and polar solvents.

24. The method as claimed in claim 18, wherein the ether or the ester of methylbutadiene used in step 4 is a 3-methoxy-1-methylbutadiene or a 3-trimethylsilyloxy-1-methylbutadiene.

25. The method as claimed in claim 18, wherein the condensation in step 4 is carried out in the presence of a Lewis acid chosen from zinc chloride, titanium tetrachloride, boron trifluoride, or trityl salts.

26. The method as claimed in claims 18, wherein a polar solvent chosen from nitroalkanes and chlorinated solvents is used.

27. The method as claimed in claim 18, wherein the fifth step is carried out in the presence of an inorganic acid chosen from hydrochloric acid, hydrobromic acid or sulfuric acid.

28. The method as claimed in claim 6, wherein a molar ratio of copper (I) salt to ethynyl-retro-α-ionol acetate of about 1% is used.

29. The method as claimed in claim 6, wherein the concentration of propargyl acetate in the reaction solvent is about 0.5 mol per liter.

30. The method as claimed in claim 12, wherein the temperature is about 100° C.

31. The method as claimed in claim 1, wherein the third step is carried out in the presence of an acid in a ketone solvent or in an aromatic solvent which is halogenated.

32. A method for preparing vitamin A, wherein in a first step β-ionone is isomerized to retro-α-ionone in the presence of a strong base chosen from alkali metal alcoholates or alkali metal hydroxides in a polar aprotic solvent, in a second step ethynylation of the compound obtained in the first step is carried out in the presence of magnesium or lithium acetylide to form ethynyl-retro-α-ionol, in a third step acetylation of the ethynyl-retro-α-ionol is carried out by bringing the ethynyl-retro-α-ionol into contact with acetic anhydride or acetyl chloride in the presence of a tertiary amine, in a fourth step the compound obtained in step three is condensed with an ether or an ester of methylbutadiene in the presence of a Lewis acid and in a fifth step the compound obtained in step four is isomerized in the presence of an inorganic acid selected from the group consisting of hydrochloric acid, hydrobromic acid and sulfuric acid.

33. The method as claimed in claim 18, wherein the solvent used is chosen from ethers and aromatic solvents.

* * * * *

UNITED STATES PATENT AND TRADEMARK OFFICE
CERTIFICATE OF CORRECTION

PATENT NO. : 6,384,270 B1
DATED : May 7, 2002
INVENTOR(S) : Ancel et al.

It is certified that error appears in the above-identified patent and that said Letters Patent is hereby corrected as shown below:

Column 10,
Line 2, delete "retroα" and insert -- retro-α --.
Lines 18-23, delete the first formula in claim 14 " 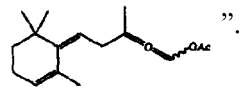 ".

Line 42, delete "ß-ionbne" and insert -- ß-ionone --.

Signed and Sealed this

Eighth Day of July, 2003

JAMES E. ROGAN
*Director of the United States Patent and Trademark Office*